(12) United States Patent
Haslacher

(10) Patent No.: US 10,780,299 B2
(45) Date of Patent: *Sep. 22, 2020

(54) SKINCARE SYSTEM

(71) Applicant: Pour Moi Beauty, LLC, Upland, CA (US)

(72) Inventor: Ulrike Haslacher, Upland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/594,213

(22) Filed: Oct. 7, 2019

(65) Prior Publication Data

US 2020/0030639 A1  Jan. 30, 2020

Related U.S. Application Data

(63) Continuation of application No. 14/609,400, filed on Jan. 29, 2015, now Pat. No. 10,485,997.

(60) Provisional application No. 61/933,154, filed on Jan. 29, 2014.

(51) Int. Cl.
*A61K 8/04* (2006.01)
*A61Q 19/00* (2006.01)
*A61Q 19/08* (2006.01)

(52) U.S. Cl.
CPC .............. *A61Q 19/00* (2013.01); *A61K 8/042* (2013.01); *A61K 2800/884* (2013.01); *A61Q 19/08* (2013.01)

(58) Field of Classification Search
CPC ...................................................... A61K 8/042
See application file for complete search history.

(56) References Cited

U.S. PATENT DOCUMENTS

| | | |
|---|---|---|
| 6,843,995 B2 | 1/2005 | Golz-Berner et al. |
| 7,060,693 B1 | 6/2006 | Dumas et al. |
| 7,349,857 B2 | 3/2008 | Manzo |
| 2002/0012640 A1 | 1/2002 | Mohammadi et al. |
| 2004/0191330 A1 | 9/2004 | Keefe et al. |
| 2004/0202685 A1 | 10/2004 | Manzo |
| 2005/0074483 A1 | 4/2005 | Lange |
| 2010/0098794 A1 | 4/2010 | Armand |
| 2013/0078294 A1 | 3/2013 | Alexiades-Armenakas |

FOREIGN PATENT DOCUMENTS

| | | |
|---|---|---|
| CN | 1468088 A | 1/2004 |
| DE | 102009008940 A1 | 8/2010 |
| JP | H07270396 A | 10/1995 |
| JP | H08143421 A | 6/1996 |
| JP | 2000302660 A | 10/2000 |
| JP | 2009137909 A | 6/2009 |

(Continued)

OTHER PUBLICATIONS

Office Action dated Jun. 3, 2020, KR Patent Application No. 10-2016-7023798.

(Continued)

*Primary Examiner* — Benjamin J Packard
(74) *Attorney, Agent, or Firm* — LeonardPatel PC

(57) ABSTRACT

A system and method may allow a person to rotate a skin care product based on the current climate to help skin transition to and react to changes in temperature and humidity the air. For example, each moisturizer may be formulated to support skin needs for a specific climate, such as tropical climate (i.e., humid and hot air), a desert climate (i.e., dry and hot air), a temperate climate (i.e., normal and mild air), and/or a polar climate (i.e., cold and dry air).

4 Claims, 1 Drawing Sheet

(56) References Cited

FOREIGN PATENT DOCUMENTS

| JP | 2017017453 | A  | 1/2017  |
|----|------------|----|---------|
| WO | 2004103302 | A2 | 12/2004 |
| WO | 2009127058 | A1 | 10/2009 |
| WO | 2009127058 |    | 11/2010 |

OTHER PUBLICATIONS

Office Action dated Jul. 12, 2020, BR Patent Application No. 112016017525 5.
"1000 Cream", Jan. 2012, https://www.gnpd.com/sinatra/recordpage/1721671/from_search/tJ8phDUttk/?page=1.
"1010 Serum", Jan. 2012, https://www.gnpd.com/sinatra/recordpage/1721672/from_search/lltrgl5chv/?page=1.
"1060 Toning Lotion", Jan. 2012, https://gnpd.com/sinatra/recordpage/1716268/from_search/ARnfWqy2YF/?page=1.
"Concentrated Perfector Serum", Jan. 2012, https://www.gnpd.com/sinatra/recordpage/1686917/from_search/IP6ngVijkN/page=1.
"Creme Luxe 2 White Truffle Age-Defy Face Cream", Oct. 2007, https://www.gnpd.com/sinatra/recordpage/798613/from_search/k0xtqECjHk/?page=1.
"Encyclopedia of Cosmetics", Maruzen Co., Ltd., Society of Chemists of Japan, Apr. 25, 2005, pp. 43-48, 325, 430-432, 441-442, 529, 545-546, 686, 707-709, 764-765.
"Examination Report", dated Jan. 11, 2018, Australian Patent Appln. No. 2015210893.
"Examination Report", dated Jan. 16, 2017, Australian Patent Appln No. 2015210893.
"Examination Report", dated Jul. 28, 2017, Australian Patent Appln. No. 2015210893.
"Examination Report", dated Nov. 3, 2017, Australian Patent Appln. No. 2015210893.
"Examiner's Report", dated Dec. 11, 2017, Canadian Patent Appln. No. 2,937,516.
"Extended European Search Report", dated Jul. 5, 2017, EP Appln. No. 15742930.9.
"Face Serum", Apr. 2012, https://www.gnpd.com/sinatra/recordpage/1773311/from_search/cAtiTHEFMy/?page=1.
"Line Smoothing Toning Lotion", Sep. 13, 2019, https://www.gnpd.com/sinatra/recordpage/2197686/from_search/BwSRyJmjMr/?page+1.
"Night Nutritive Cream Regenerating & Detoxifying", Nov. 2012, https://www.gnpd.com/sinatra/recordpage/1937678/from_search/V16yHXNFX2/?page=1.
"Notice of Reasons for Rejection", dated Nov. 6, 2018, JP Patent Application No. 2017-226536.
"Office Action", dated Apr. 4, 2018, Chinese Appln. No. 201580010597.0.
"Office Action", dated Jan. 19, 2017, Israeli Appln. No. 246946.
"Office Action", dated Jul. 25, 2017, Japanese Appln. No. 2016-538833.
"Office Action", dated Mar. 29, 2017, Japanese Appln. No. 2016-538833.
"Office Action", dated May 12, 2017, Canadian Patent Appln. No. 2,937,516.
"P299 Oil-Free Anti-Wrinkle Serum", Sep. 2012, https://www.gnpd.com/sinatra/recordpage/1839718/from_search/kHRm7hilcj/?page=1.
"Recovery Day Cream SPF 15", Aug. 2013, https://www.gnpd.com/sinatra/recordpage/2137843/from_search/KHNyqfzDDA/?page=1.
"Rejuvenate 3-Step Layering Set" https://intraceuticals.com/rejuvenate-3-step-layering-set.html.
Beautygeeks (http://imabeautygeek.com/2013/05/17/glow-getter-the-2nd-best-thing-ive-done-for-my-skin-again-I'm-44/, accessed Oct. 1, 2015, having a date May 17, 2013).
Benjamin J Packard, "Final Office Action", dated Mar. 7, 2019, U.S. Appl. No. 14/609,400.
Benjamin J Packard, "Non-Final Office Action", dated Oct. 2, 2018, U.S. Appl. No. 14/609,400.
Benjamin J Packard, "Notice of Allowance", dated Sep. 27, 2019, U.S. Appl. No. 14/609,400.
Benjamin J. Packard, "Final Office Action" dated Apr. 21, 2016 for U.S. Appl. No. 14/609,400.
Benjamin J. Packard, "Non-Final Office Action" dated Oct. 7, 2015 for U.S. Appl. No. 14/609,400.
Benjamin J. Packard, "Non-Final Office Action", dated Sep. 9, 2016, U.S. Appl. No. 14/609,400.
Cosmopolitan, "Top Ten Winter Moisturisers to Save Your Skin", downloaded from the internet on Dec. 6, 2018 at published in Cosmopolitan on Oct. 19, 2013.
Examination Report, dated Apr. 15, 2019, CA Patent Application No. 2,937,516.
Examination Report, dated Nov. 27, 2018, JP Patent Application 2016-538833.
Examination Report, dated Nov. 6, 2018, JP Patent Application No. 2017-226536.
Final Office Action dated Oct. 1, 2019, Japanese Patent Application No. 2016-538833.
Fujita et al., "Bulletin of Geo-Environmental Science", 2008, vol. 10, pp. 49-67.
Full Examination Report, dated Dec. 7, 2018, AU Patent Application No. 2018200337.
Hiroki Murooka, "Skincare & Makeup Lesson", Shinsei Shuppan, Inc., Part 1 pp. 18-32, Part 2 pp. 33-37, 52-74, 78-94.
http:www.snowwhiteandtheasianpear.com/2013/03/skincare-discovery-layering-multiple.html (Mar. 2013) Part 1.
http:www.snowwhiteandtheasianpear.com/2013/03/skincare-discovery-layering-multiple.html (Mar. 2013) Part 2.
Intraceuticals Blog, "Tis the Season for Joyous Skin: Only 15 Days to Go Until Beautiful Skin", downloaded from the Internet on Jan. 10, 2018 at URL< http://intraceuticals.blogspot.com.au/2013/12/only-15-days-to-go-until-beautiful-skin.html#!/2013/12/only-15-days-to-go-until-beautiful-skin.html>, posted on Dec. 11, 2013.
Intraceuticals, "Only 15 Days to Go Until Beautiful Skin", published Dec. 11, 2013, http://intraceuticals.blogspot.com/2013/12/only-15-days-to-go-until-beautiful-skin.html.
JP Office Action, dated Nov. 27, 2018, JP Patent Application No. 2016-538833.
Kikuchi at al. 'Noninvasive biophysical assessments of the efficacy of a moisturizing cosmetic cream base for patients with atopic dermatitis during different seasons'. British Journal of Dermatology. May 2008. vol. 158. No. 5.pp. 969-978, especially, Abstract; p. 976, Col. 2. para 3.
My Face My Body My Soul, "New Intraceuticals 3-Step Trial Pack!" downloaded from the internet on Jan. 10, 2018 at URL<http://www.myfacemybodymysoul.com.au/2014/08/new-intraceuticals-trial-pack/>, posted Aug. 14, 2014.
Nakagawa et al., "Smart Skincare System: Remote Skincare Advise System Using Lifelogs", Information Processing Society of Japan, vol. 52, No. 4, 1537-1551 (Apr. 2011).
Nishiyama et al., "Skin Care Products and the Skin", Journal of the Japan Society of Colour Material, 1989, vol. 62, No. 8, pp. 487-495.
Notice of Acceptance, dated Oct. 22, 2019, Australian Patent Application No. 2018200337.
Notification of Transmittal of the International Search Report, dated Apr. 15, 2015 for International Application No. PCT/US 15/13626.
Office Action, dated Sep. 30, 2019, BR Patent Application No. 112016017525 5.
Philippe Couture, "Examiner's Report", dated Jul. 30, 2018, Canadian Patent Application No. 2,937,516.
S. Von Eggelkraut-G, "Supplementary European Search Report", dated Jul. 5, 2017, Appln. No. 15742930.9.
Second Office Action, dated Feb. 3, 2019, CN Patent Application No. 2015800105970.
The Skincare Edit, "10 Tips to Save Your Skin from Cold, Dry, Winter Weather", published Jan. 8, 2014, downloaded from the internet on Dec. 6, 2018.
The Skincare Edit, "The Right Order to Apply Your Skincare and Makeup Products", https://theskincareedit.com/2010/08/19/remember-the-order-of-operations-in-math-well-this-is-like-that-but-for-your-face > published Aug. 19, 2010, downloaded from the internet on Dec. 6, 2018.

(56) References Cited

OTHER PUBLICATIONS

The Skincare Edit, 10 Tips to Save Your Skin from Cold, Dry, Winter Weather, published Jan. 8, 2014, downloaded rom the Internet on Dec. 6, 2018.

Xiaomei Zhang, Fashion Goods for Charming Lady, 1st Edition, Lijiang Publishing House, pp. 146-147, Oct. 2009.

Yoav Sin-Melia, "Office Action" issued by State of Israel—The Patent Office dated Jan. 19, 2017 for IL Application Serial No. 246946.

"Final Office Action", dated Jun. 9, 2020, JP Patent Application No. 2017-226536.

Office Action, dated Jun. 18, 2020, CN Patent Application No. 201580010597.0.

"Office Action", dated Dec. 11, 2019, CA Patent Application No. 2,937,516.

Rees, Anushka, "A Winter Skin Care Routine", published Jan. 20, 2013.

Rees, Anushka, "My Skin Care Routine—Fall 2013", published Oct. 13, 2013.

Rees, Anushka, "Summer Skin Solution", published May 19, 2013.

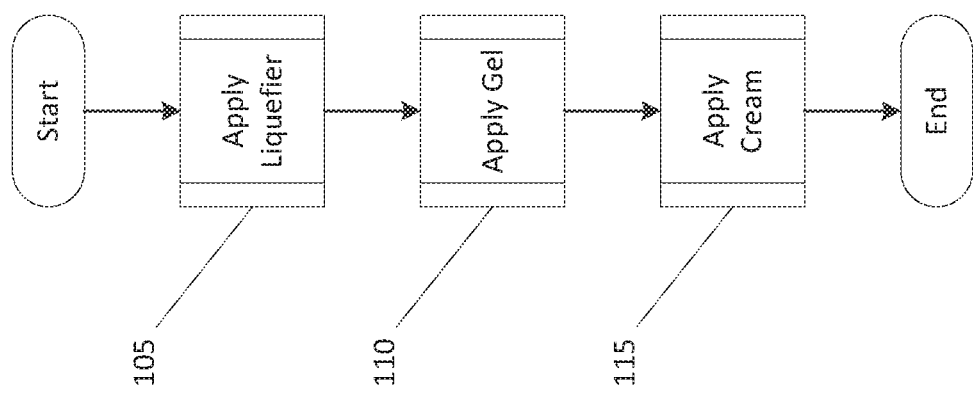

SKINCARE SYSTEM

CROSS-REFERENCE TO RELATED APPLICATIONS

This application is a continuation of U.S. patent application Ser. No. 14/609,400, filed Jan. 29, 2015, and claims the benefit of priority to U.S. Provisional Patent Application No. 61/933,154, titled SKINCARE SYSTEM, filed Jan. 29, 2014, the disclosure of which is hereby incorporated by reference herein in its entirety.

FIELD

The present invention generally relates to a skincare system and, more particularly, to a three step skincare system to help a person's skin adapt to changes in climate and environment.

BACKGROUND

Every three to six months, climate changes everywhere in the world and the change of temperature and humidity in the air not only cause the weather to change, but also cause changes in a person's skin. For instance, when the climate changes, the amount of humidity in the air changes, and increased or decreased humidity causes more or less moisture to be drawn from the air into skin. For example, when the humidity in the air decreases due to a fall in temperature and the reduced capacity for air to hold moisture, for example, a person's skin dries out and stresses.

Eventually, the skin adjusts by initiating multiple chemical reactions. For instance, the skin may try to stay warm or cool and deal with the moisture loss caused by decreased humidity (e.g., dry skin) or excessive humidity in the air (e.g., sweating). Many negative skin problems can occur due to this adjustment. For example, the appearance of fine lines, wrinkles, irritations, breakouts, etc., may be caused or accelerated.

Because climate affects a person's skin in significant ways, the skin may look and feel its best in the summer and in different seasons, the skin may have different needs and may not have the desired appearance. The same is true for different locations. For example, the skin experiences a dry climate (e.g., in the desert) differently than it experiences a humid climate (e.g., in the tropics).

The skin's ability to absorb and benefit from skincare products varies with the changing temperature and humidity, often making products less effective when the air around the person changes in temperature and humidity. Furthermore, many people travel for work and pleasure, frequently exposing their skin to different climates. Because the face is not protected by cloth, the impact of the changing climate may cause the skin to struggle, and stress the skin, when it adjusts to climate changes.

SUMMARY

Certain embodiments of the present invention may provide solutions to the problems and needs in the art that have not yet been fully identified, appreciated, or solved by current skin care systems. Some embodiments of the present invention provide a novel system and method that allows a person to rotate a skin care product based on the current climate to help skin transition and react to changes in the temperature and moisture of the air. For example, each moisturizer may be formulated to support skin needs for a specific climate, such as tropical climate (i.e., humid and hot air), a desert climate (i.e., dry and hot air), a temperate climate (i.e., normal and mild air), and polar climate (i.e., cold and dry air). Furthermore, specific moisturizer types may be used based on the season in areas where the temperature and/or humidity changes during the year.

The method of changing moisturizers as climate changes of some embodiments helps the skin to stay moisturized and hydrated. Because the body is mostly made of water, the body's ability to stay hydrated and maintain water is important. As with the body generally, skin tries to stay moisturized. However, due to the direct exposure to air, the skin has more of a challenge in maintaining hydration levels. With the system and method discussed herein with respect to some embodiments, the hydration of the skin may be improved.

In one embodiment, a three-step skincare system is provided. The first two steps include moisturizing products containing a proprietary blend of moisturizing and anti-aging properties to help skin maintain hydration and youthful appearance. These products are not necessarily formulated for a specific climate, but instead focus on delivering the active ingredients deep into the skin. However, the third step includes multiple moisturizers, where each product is specially formulated for a specific climate to help skin protect against dry air or help skin to benefit more from humidity in the air.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which:

FIG. 1 is a flow diagram illustrating a process for a skin care application, according to an embodiment of the present invention.

DETAILED DESCRIPTION OF THE EMBODIMENTS

Some embodiments of the present invention pertain to a three-step skin care system.

FIG. 1 is a flow diagram 100 illustrating a process for a skin care application, according to an embodiment of the present invention. The process begins at 105 with applying a hydrating liquefier to rejuvenate and balance a person's skin. At 110, a hydrating gel is applied to the person's skin to repair and renew the skin. At 115, based on the climate, an appropriate hydrating cream is applied to the skin for protection. The cream may be rotated according to the climate, e.g., a polar formulation for winter climates, a temperate formulation for fall and spring climates, a desert formulation for summer and/or dry climates, and a tropical formulation for summer and/or humid climates.

Each step may include one or more of the following ingredients, with benefits listed below:

A Techno-Blend: an advanced blend of multiple hyaluronic acids of different molecular weights with purest white truffle extract rich in amino acids, minerals and valuable sugar ingredients. The blend is moisturizing and rich in anti-aging properties for a global, climate sensitive, anti-aging strategy.

Palmitoyl tripeptide-38: a powerful anti-wrinkle peptide, which stimulates the synthesis of six major constituents of the skin matrix and dermalepidermal junction (collagen I, III, IV, fibronectin, hyaluronic acid and laminin 5). This ingredient also evens out skin relief and smoothens wrinkles from the inside by rebuilding the skin.

Ethylene/Acrylic acid copolymer: soft-focus benefit with immediate optical effect by reflecting the light to minimize the appearance of fine wrinkles and other skin defaults.

Methyl methacrylate crosspolymer: polymeric powder made up of hollow hemi-spheres with smooth surface, it brings soft and powdery feel. This has a mattifying effect due to lipid absorption and the suppression of specular reflection (immediate optical effect).

Vitamins A, C, E complex (ascorbyl palmitate, tocopherol, retinyl palmitate): vitamin A promotes the enzyme activity of the skin and increases its collagen content, and is thus able to regenerate skin. Vitamins E and C represent an effective combination to act as antioxidants, free radical scavengers and peroxide neutralizers, in this way helping to prevent skin ageing as a result of UV radiation.

Glycerin: high moisturizing agent, traps the water molecules thanks to its hygroscopic properties.

D-Panthenol: also named pro-vitamin B5, has moisturizing, barrier restructuring and soothing properties.

Thiotaine (Ergothioneine): skin brightener, and powerful antioxidant, which traps the free radicals responsible of premature ageing.

Polysaccharide extracted from oat (Avena Sativa Kernel Extract): immediate tensing effect.

Purified oat extract: very high molecular weight, immediate tightening effect for lifting action.

Shea butter: nourishing properties.

Fomes Officinalis extract: pore refiner.

Seaweed extract (Chlorella vulgaris extract): prevents the appearance of dark circles by stimulating peri-ocular cutaneous microcirculation. Acts in synergy with hyaluronic acids complex and boosts cutaneous tonicity and firmness by stimulating the synthesis of dermal proteins.

Myrtle extract: limits the appearance of signs ageing by favoring the synthesis of SIRT-1 (longevity proteins) and inhibiting the glycation of collagen, an irreversible reaction responsible for tissue regeneration.

Diamond sparkles: made of two marine polymers and containing diamond powder.

Natural sucroesters: for a gelified and transparent O/W emulsion, characterized by a rich feel touch and a slow spread, ideal for massage. In contact with water, this gel transforms into a milky emulsion easy to rinse off.

Sugar: exfoliating, gives soapless cleanser & peel the honey color to the product.

Silica: transparent exfoliating particles.

It should be appreciated that each step may also include a unique technology blend—Response du Climat®. This blend constructs a harmonic microenvironment within the skin that is sensitive to all different climates. This unique delivery system places and activates powerful, scientifically proven to work moisturizing and anti-aging ingredients throughout the skin layers while protecting the skin against water loss known as TEWL (Trans Epidermal Water Loss) and shields the skin against pollution, environmental aggressions, and dry air.

This blend may also be loaded with precious, pure white truffles, rich in amino acids, minerals and valuable sugars and multiple hyaluronic acids of different molecule weights for a sophisticated skin hydration strategy. The blend may be enhanced with the recommended amounts of key peptides, anti-oxidants and vitamins to firm and lift skin, reduce fine lines and wrinkles, tighten skin, even out skin complexion, and brighten skin for a gentle effective anti-aging strategy.

It should be further appreciated that the blend may support skin cell ability to trap water molecules while at the same time preventing additional water loss stimulated by humid air, dry air, cold air, or hot air, leaving skin looking firm, plump, hydrated, and stress free. The blend also acts as an accelerated carrier and delivery system to other key ingredients such as anti-oxidants, vitamins, and peptides, which are scientifically proven to work for younger, vibrant, and healthier looking skin. The blend further integrates and synergizes with the changing air/climate surrounding the skin for a beautiful, luxurious skin complexion.

It should be noted that skincare products generally do not work well unless the skincare product changes with the climate. The skin care system described herein with respect to some embodiments allows a person to change or rotate Day Cream as the climate change/rotates so skin may be optimally cared for and look and feel its best. Each Day Cream may be formulated to harmonize and synergize with the liquidized lotion of the Hydrating Balancer, step 105, and the Gelified Serum, step 110, to maximize the moisturizing and anti-aging property distribution within the skin. By using the three step skincare system daily, a person can achieve excellent beauty results and prevent irritations and breakouts while providing optimal care and protection for skin in all climates and conditions.

The skincare system of some embodiments not only accounts for ongoing climate challenges for the skin, but also solves the problem by creating a techno-blend and using a three step process that uniquely rotates the day creams as climate changes either when a person travels, the season changes, or for any other reason.

It will be readily understood that the components of various embodiments of the present invention, as generally described and illustrated in the FIGURES herein, may be arranged and designed in a wide variety of different configurations. Thus, the detailed description of the embodiments of the present invention, as represented in the attached FIGURES, is not intended to limit the scope of the invention as claimed, but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with elements in configurations different than those that are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

What is claimed is:

1. A process for skin care, comprising:
    applying a hydrating liquefier to skin, the hydrating liquefier configured to rejuvenate and balance the skin;
    applying a hydrating gel to the skin, the hydrating gel configured to repair and renew the skin; and
    selecting and applying a hydrating cream, the hydrating cream being selected according to a climate-specific formulation, the hydrating cream configured to protect the skin, wherein
    each of the one or more steps comprises a fungi extract blend comprising of white truffle extract, rich in amino acids, minerals and valuable sugars and multiple hyaluronic acids of different molecule weights, and
    the fungi extract blend further comprises peptides, antioxidants and vitamins to firm and lift skin, reduce fine lines and wrinkles, tighten skin, even out skin complexion, and brighten skin.

2. The process of claim 1, the selected hydrating cream having a climate-specific formulation selected from the group of formulations comprising a polar formulation configured for winter climates, a temperate formulation configured for fall and spring climates, a desert formulation configured for summer and dry climates, and a tropical formulation for summer and humid climates.

3. The process of claim 2, wherein the selected hydrating cream is formulated and configured to mix with the hydrating liquefier to synergistically enhance effects of the hydrating cream and the hydrating liquefier on the skin.

4. The process of claim 2, wherein the selected hydrating cream is formulated and configured mix with the hydrating gel to synergistically enhance effects of the hydrating gel and the hydrating liquefier on the skin.

* * * * *